United States Patent [19]

Flockerzi et al.

[11] Patent Number: 5,346,904

[45] Date of Patent: Sep. 13, 1994

[54] SULPHONYL COMPOUND

[75] Inventors: Dieter Flockerzi; Kurt Klemm, both of Allensbach, Fed. Rep. of Germany

[73] Assignee: BYK Gulden Lomberg Chemische Fabrik GmbH, Constance, Fed. Rep. of Germany

[21] Appl. No.: 945,975

[22] PCT Filed: May 14, 1991

[86] PCT No.: PCT/EP91/00895

§ 371 Date: Nov. 4, 1992

§ 102(e) Date: Nov. 4, 1992

[87] PCT Pub. No.: WO91/17991

PCT Pub. Date: Nov. 28, 1991

[30] Foreign Application Priority Data

May 16, 1990 [CH] Switzerland ............... 1658/90

[51] Int. Cl.⁵ ................. A61K 31/445; C07D 471/04
[52] U.S. Cl. ........................ 514/292; 546/81; 546/92
[58] Field of Search ............ 546/81, 92; 514/292

[56] References Cited

U.S. PATENT DOCUMENTS 3,899,494 8/1975 Ott et al. .................. 260/287 R
4,087,530 5/1978 Ott et al. .................. 424/258

FOREIGN PATENT DOCUMENTS 0247971 12/1987 European Pat. Off. ............. 546/81

OTHER PUBLICATIONS

Morrison & Boyd, Allyn and Bacon, Inc. Boston, second edition, 1971, pp. 751–753.

*Primary Examiner*—Marianne M. Cintins
*Assistant Examiner*—Phyllis G. Spivack
*Attorney, Agent, or Firm*—Jacobson, Price, Holman & Stern

[57] ABSTRACT

Compound of the formula I wherein the substituents have the meanings given in the description, are new active bronchodilators.

9 Claims, No Drawings

SULPHONYL COMPOUND

SCOPE OF APPLICATION OF THE INVENTION

The invention relates to new sulphonyl compounds, processes for their preparation, their use and medicaments containing them. The compounds according to the invention are used in the pharmaceutical industry for the preparation of medicaments.

KNOWN TECHNICAL BACKGROUND

Substituted benzo-naphthyridines which are distinguished by a pronounced inhibition of blood platelet aggregation are described in DE-OS 21 23 328 and in U.S. Pat. No. 3,899,494. The use of the compound with the proposed INN benafentrin, which falls under these protective rights, as a bronchodilator and for the treatment of inflammatory diseases of the respiratory tract is disclosed in European Patent Application 247 971.

DESCRIPTION OF THE INVENTION

It has now been found that the compounds described in more detail below, which differ from the compound benafentrin in particular by the sulphonyl substitution instead of the acetyl substitution on the amino group, have surprising and particularly advantageous properties.

The invention thus relates in a first aspect to compounds of the formula I

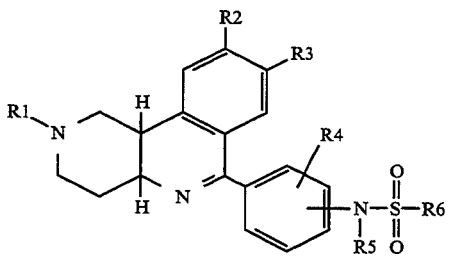

wherein
R1 denotes 1-4C,-alkyl,
R2 denotes hydrogen (H), 1-4C-alkyl or 1-4C-alkoxy,
R3 denotes hydrogen (H), 1-4C-alkyl or 1-4C-alkoxy,
R4 denotes hydrogen (H), methyl or methoxy,
R5 denotes hydrogen (H) or 1-4C-alkyl and
R6 denotes 1-4C-alkyl, phenyl or substituted phenyl with one or two identical or different substituents from the group comprising 1-4C-alkyl, 1-4C-alkoxy, hydroxyl and halogen,
and their salts.

1-4C-Alkyl represents straight-chain or branched alkyl radicals having 1 to 4 carbon atoms. Examples which may be mentioned are the butyl, iso-butyl, sec.-butyl, tert.-butyl, propyl, isopropyl, ethyl and in particular the methyl radical.

1-4C-Alkoxy radicals contain one of the abovementioned 1-4C-alkyl radicals in addition to the oxygen atom. The methoxy radical is preferred.

Halogen in the context of the present invention is bromine, chlorine or fluorine.

Examples which may be mentioned of substituted phenyl radicals R6 are the radicals: 4-methylphenyl, 4-tert.-butylphenyl, 4-methoxyphenyl, 4-fluorophenyl, 4-chlorophenyl, 2,5-dichlorophenyl and 4-hydroxyphenyl.

Preferred possible salts for compounds of the formula I are all the acid addition salts. Salts which may be mentioned in particular are the pharmacologically tolerated salts of the inorganic and organic acids usually used in galenics. Salts which are not pharmacologically tolerated and may initially be obtained, for example, as process products during preparation of the compounds according to the invention on an industrial scale are converted into pharmacologically tolerated salts by processes which are known to the expert. Examples of such suitable salts are water-soluble and water-insoluble acid addition salts, such as the hydrochloride, hydrobromide, hydriodide, phosphate, nitrate, sulphate, acetate, citrate, gluconate, benzoate, hibenzate, fendizoate, butyrate, sulphosalicylate, maleate, laurate, realate, fumarate, succinate, oxalate, tartrate, aresonata, embonate, metembonate, stearate, rosylate, 3-hydroxy-2-naphthoate or mesylate.

Compounds of the formula I which are to be singled out are those in which
R1 denotes 1-4C-alkyl,
R2 denotes 1-4C-alkoxy,
R3 denotes 1-4C-alkoxy,
R4 denotes hydrogen or methyl,
R5 denotes hydrogen or 1-4C-alkyl and
R6 denotes 1-4C-alkyl, phenyl or substituted phenyl with one substituent from the group comprising 1-4C-alkyl, 1-4C-alkoxy and halogen,
and their salts.

Compounds of the formula I which are to be singled out in particular are those in which
R1 denotes methyl,
R2 denotes methoxy,
R3 denotes methoxy and
R4 denotes hydrogen or methyl, the radical -N(R5)SO2R6 is in the 4-position of the phenyl radical bonded in the 6-position on the benzo-naphthyridine ring,
R5 denotes hydrogen, methyl or ethyl and
R6 denotes methyl, 4-methylphenyl, 4-methoxyphenyl or 4-fluorophenyl,
and their salts.

The benzo-naphthyridine ring has (at positions 4a and 10b) two chirality centers. The invention therefore relates to all the conceivable enantiomers and diastereomers, as well as the racemates and mixtures thereof. Those compounds of the formula I in which the hydrogen atoms positions 4a and 10b are in the cis-position are preferred.

The enantiomerically pure cis-compounds which are mirror images of one another and rotate linearly polarized light in the (+) or (−) direction [(+)-enantiomer and (−)-enantiomer] are particularly preferred. The trans-compounds are separated from the (diastereomeric) cis-compounds—in the same way as the (+)- and (−)-enantiomers are separated—in a manner with which the expert is familiar, e.g. as described in European Patent Application 247 971.

Those compounds of the formula I which are derived from compounds of the formula II which have the same absolute configuration as the compound (−)-cis-6-(4-aminophenyl )-8,9-dimethoxy-1,2,3,4,4a, 10b-hexahydro-2-methylbenzo[c][1,6]-naphthyridine with the optical rotation of

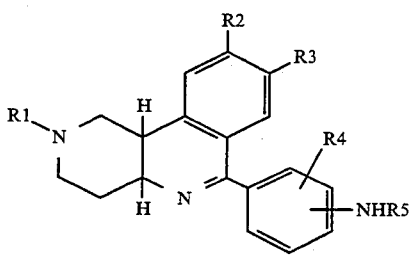

(c=1, chloroform), are particularly preferred in this connection.

The invention furthermore relates to a process for the preparation of the compounds of the formula I according to the invention and their salts. process is characterized in that a) compounds of the formula II

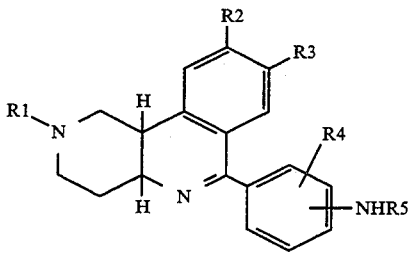

wherein R1, R2, R3, R4 and R5 have the abovementioned meanings, are reacted with sulphonyl compounds of the formula III

wherein R6 has the abovementioned meaning and X represents a suitable leaving group, or in that b) to prepare compounds I in which R5 denotes 1-4C-alkyl, compounds of the formula I in which R5 denotes hydrogen are alkylated with an alkylating agent of the formula IV

wherein R5 denotes 1-4C-alkyl and Y denotes a leaving group, or in that c) compounds of the formula V

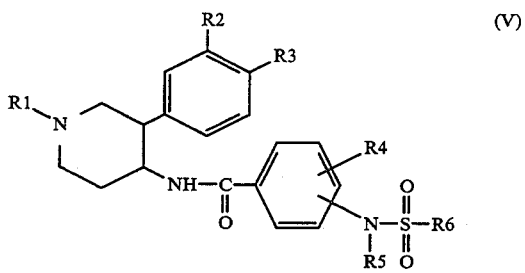

wherein R1, R2, R3, R4, R5 and R6 have the abovementioned meanings, are subjected to a cyclocondensation reaction, and in that, if desired, the compounds I obtained according to a), b) or c) are then converted into their salts, or in that, if desired, the compounds I are then liberated from resulting salts of the compounds I.

The reaction of the compounds II with the compounds III is carried out in inert solvents in a manner known to the expert for the preparation of sulphonamides. The leaving group X is preferably a halogen atom, in particular a chlorine atom. The reaction is preferably carried out in the presence of an auxiliary base, e.g. an organic amine, such as triethylamine or pyridine, or e.g. a carbonate, such as potassium carbonate or sodium carbonate.

The N-alkylation according to process variant b) is carried out in a manner with which the expert is familiar, if appropriate under phase transfer conditions, preferably in the presence of suitable bases or after prior deprotonation of the compounds I where R5=hydrogen.

Possible deprotonating agents are, above all, those agents for which the acidity of the proton on the nitrogen is high enough to achieve anion formation. In addition to organometallic compounds, such as e.g. butyllithium, examples which may be mentioned are metal hydrides, in particular sodium hydride, or alkali metal alcoholates, e.g. sodium methylate or potassium tert.-butylate, or alkali metal hydroxides, e.g. sodium hydroxide or potassium hydroxide, or alkali metal carbonates, e.g. sodium carbonate.

The leaving group Y of the compounds IV is a group which is easily split off during the reaction of Y - R5 with the deprotonated I, for example a halogen atom, such as chlorine, bromine or iodine, or the alkyl-sulphate group.

The deprotonation and subsequent N-alkylation are carried out in inert, anhydrous solvents, such as are suitable for working with powerful deprotonating agents, or in water-solvent mixtures, such as are employed when working under phase transfer conditions. Examples which may be mentioned are open-chain or cyclic ethers, such as diethyl ether, dioxane or tetrahydrofuran, or solvents, such as DMF or DMSO. Examples of water/solvent mixtures which may be mentioned are mixtures of water with chloroform, methylene chloride or benzene. The reaction is preferably carried out under mild reaction conditions at temperatures of about or below 0° C.

The cyclocondensation according to process variant c) is carried out in manner which is known per se to the expert by the Bischler-Napieralski method in the presence of a suitable condensing agent, such as, for example, polyphosphoric acid, phosphorus pentachloride, phosphorus pentoxide or preferably phosphorus oxytrichloride, in a suitable inert solvent, e.g. in a chlorineted hydrocarbon, such as chloroform, or in a cyclic hydrocarbon, such as toluene or xylene, or another inert solvent, such as acetonitrile, or without a further solvent using an excess of condensing agent, preferably at elevated temperature, in particular at the boiling temperature of the solvent or condensing agent used.

The compounds of the formula II where R5=hydrogen are known from DE-OS 21 23 328, U.S. Pat. No. 3,899,494 or EP-A-247 971, or they can be prepared in a manner analogous to that described in the above specifications. Compounds II where R5=1-4C-alkyl can be prepared from the compounds II where R5=hydrogen by alkylation in a manner with which the expert is familiar.

The compounds of the formula V are obtained in a manner which is known per se from the compounds VI and VII according to the following equation

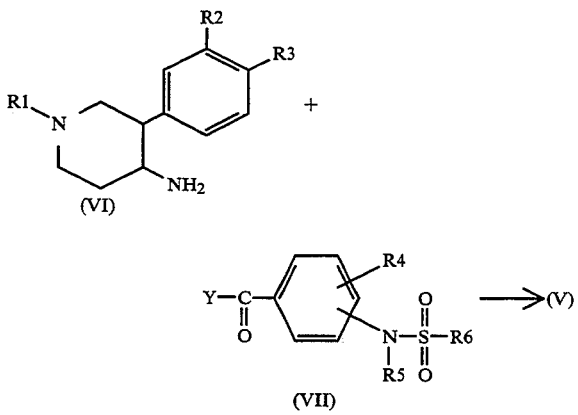

wherein R1, R2, R3, R4, R5 and R6 have the above-mentioned meanings and Y represents a leaving group, for example a chlorine atom.

The compounds VI are known e.g. from DE-OS 21 23 328 or EP-A-247 971, or they can be prepared in an analogous manner. The compounds VII are likewise known, or can be prepared in a manner which is known to the expert.

To prepare enantiomerically pure compounds I, the separation of the trans-compounds from the cis-compounds as well as the separation of the (+)- and (−)-enantiomers is carried out preferably on the step of the compounds II which are known from EP-A-247 971 or which can be prepared and separated as described there.

The following examples illustrate the invention in more detail, without limiting it. The invention preferably relates to the compounds of the general formula I listed by name in the examples and the salts of these compounds. M.p. denotes melting point, and the abbreviation h is used for hour(s) and the abbreviation min for minutes. Decomp. represents decomposition. "Ether" is understood as meaning diethyl ether.

EXAMPLES 1.
rac-cis-8,9-Dimethoxy-1,2,3,4,4a,10b-hexahydro-2-methyl-6-(4-methylsulphonamidophenyl)-benzo[c][1,6-]naphthyridine A solution of 0.6 ml methanesulphonyl chloride in 3 ml absolute dioxane is added dropwise to a solution of 2.1 g rac-cis-6-(4-aminophenyl)-8,9-dimethoxy-1,2,3,4,4a, 10b-hexahydro-2-methyl-benzo[c ][1,6]naphthyridine in 20 ml absolute pyridine, and the mixture is then stirred at 60° C. for a further 3 h. After cooling, the mixture is poured onto 100 ml of an ice/water mixture, rendered alkaline with dilute sodium hydroxide solution and extracted with n-butanol. After the n-butanol has been evaporated off, the residue which remains is extracted with methylene chloride and the organic phase is dried over sodium sulphate and then concentrated. 2.4 g of the title compound are obtained as the residue and are converted into the dihydrochloride with ethereal HCl, and the product is recrystallized from non-dried methanol. Yield: 2.3 g of the title compound as the dihydrochloride hydrate. M.p. 239°–240° C. (decomposition).

2.
rac-cis-8,9-Dimethoxy-1,2,3,4,4a,10b-hexahydro-2-methyl-6-[4-(p-toluenesulphonamido)-phenyl]-benzo[c][1,6]naphthyridine The title compound is obtained analogously to Example 1 if p-toluenesulphonyl chloride is employed instead of methanesulphonyl chloride. M.p. 219°–221° C. (dihydrochloride hydrate).

3.
rac-cis-8.9-Dimethoxy-1,2,3,4,4a,10b-hexahydro-2-methyl-6-[4-methyl-3-(p-toluenesulphonamido)-phenyl]-benzo[c][1,6]naphthyridine 3.9 g rac-cis-3-(3,4-dimethoxyphenyl)-1-methyl-4-[4-methyl-3-(p-toluene-sulphonamido)-benzamido]-piperidine are heated at the boiling point under reflux in 50 ml phosphorus oxytrichloride for 3 h. After the excess phosphorus oxytrichloride has been distilled off, the residue is partitioned between methylene chloride and 2 N sodium hydroxide solution, and the organic phase is washed with water and dried over sodium sulphate. After the methylene chloride has been distilled off, the residue is purified by silica gel chromatography. The main product fraction which has been separated off is concentrated and the solid residue is recrystallized from ethyl acetate/petroleum ether. 2.6 g of the title compound are obtained as yellowish crystals of m.p. 206°–210° C. (decomp.).

The starting compound rac-cis-3-(3,4-dimethoxyphenyl)-1-methyl-4-[4-methyl-3-(p-toluenesulphonamido)-benzamido]-piperidine is obtained by reaction of 4.6 g 4-methyl-3-(p-toluenesulphonamido)-benzoyl chloride with 3.0 g rac-cis-4-amino-3-(3,4-dimethoxyphenyl)-1-methylpiperidine and 4 ml triethylamine in 50 ml anhydrous methylene chloride. After extraction by shaking with NaHCO3 solution, drying of the organic phase over sodium sulphate and concentration, the residue is recrystallized from methanol. Yield: 4.2 g, m.p. 142°–146° C.

4.
rac-cis-8,9-Dimethoxy-1,2,3,4,4a,10b-hexahydro-2-methyl-6-[2-(p-toluenesulphonamido)-phenyl]-benzo[c][1,6]naphthyridine The title compound is obtained analogously to Example 3 from 4.5 g rac-cis-3-(3,4-dimethoxyphenyl )-1-methyl-4-[2-(p-toluenesulphonamido )-benzamido]-piperidine and 30 ml phosphorus oxytrichloride. Yield: 3-3 g brownish crystals.

The starting compound rac-cis-3-(3,4-dimethoxyphenyl)-1-methyl-4-[2-(p-toluenesulphonamido)-benzamido]-piperidine is obtained analogously to Example 3 from 2-(p-toluenesulphonamido)-benzoyl chloride and the corresponding piperidine. Yield: 70%.

5.
rac-cis-8.9-Dimethoxy-1,2,3,4,4a,10b-hexahydro-2-methyl-6-[4-(p-methoxyphenylsulphonamido)-phenyl]-benzo[c][1,6]naphthyridine The title compound is obtained analogously to Example 1 if p-methoxyphenylsulphonyl chloride is employed. Yield: 66%, m.p. 210°–217° C. (as the carbonate hydrate crystallized from methanol).

Alternatively, the title compound is obtained analogously to Example 3 if rac-cis-3-(3,4-dimethoxyphenyl)-1-methyl-4-[(4-p-methoxyphenylsulphonamido)-benzamido]-piperidine is subjected to cyclocondensation.

The starting compound is obtained analogously to Example 3 if 4-(p-methoxyphenylsulphonamido)-benzoyl chloride is employed.

6. rac-cis-8.9-Dimethoxy-1,2,3,4,4a,10b-hexahydro-2-methyl-6-[4-(p-fluorophenylsulphonamido)-phenyl]-benzo[c][1,6]naphthyridine The title compound is obtained analogously to Example 3 from rac-cis-3-(3,4-dimethoxyphenyl)-1-methyl-4-[(p-fluorophenylsulphonamido)-benzamido]-piperidine. Yield: 69%, m.p. 163°–165° C.

The starting compound is obtainable analogously to Example 3 from 4-(p-fluorophenylsulphonamido)-benzoyl chloride. Yield: 60%, m.p. 108°–113° C.

7. rac-cis-8,9-Dimethoxy-1,2,3,4,4a,10b-hexahydro-2-methyl-6-[4-(p-toluenesulphon-N-methylamido)-phenyl]-benzo[c][1,6]naphthyridine The title compound is obtained analogously to Example 3 from rac-cis-3-(3,4-dimethoxyphenyl)-1-methyl-4-[(p-toluenesulphon-N-methylamido)benzamido]-piperidine; yield: 53%, m.p. 157°–158° C. (from methanol/ether).

The starting compound is obtainable analogously to Example 3 from 4-(p-toluenesulphon-N-methylamido)-benzoyl chloride.

8. rac-cis-8.9-Dimethoxy-1,2,3,4,4a,10b-hexahydro-2-methyl-6-[4-(p-toluenesulphon-N-ethylamido)-phenyl]-benzo[c][1,6]naphthyridine The title compound is obtained analogously to the above example if instead of the N-methyl compounds the corresponding N-ethyl compounds are employed. Yield: 71%, m.p. 160°–166° C. (carbonate).

9. (−)-cis-8,9-Dimethoxy-1,2,3,4,4a,10b-hexahydro-2-methyl-6-[4-(p-toluenesulphonamido)-phenyl]-benzo[c][1,6]naphthyridine The title compound is obtained analogously to Example 1 if (-)-cis-6-(4-aminophenyl)-8,9-dimethoxy-1,2,3,4,4a,10b-hexahydro-2-methyl-benzo[c][1,6]naphthyridine $[\alpha]^{22}_{578Hg} = -213°$ (c=1, CHCl₃) is reacted with p-toluenesulphonyl chloride. Yield 82%, m.p. 178°–183° C. (yellowish crystals from ethyl acetate/methanol);

$[\alpha]^{22}_D = -81.6°$, $[\alpha]^{22}_{578Hg} = -81.1°$, (in each case c=1, methanol).

10. (+)-cis-8,9-Dimethoxy-1,2,3,4,4a,10b-hexahydro-2-methyl-6-[4-(p-toluenesulphonamido)-phenyl]-benzo[c][1,6]naphthyridine The title compound is obtained analogously to Example 9 if (+)-cis-6-(4-aminophenyl)-8,9-dimethoxy-1,2,3,4,4a,10b-hexahydro-2-methyl-benzo[c][1,6]naphthyridine $[\alpha]^{22}_{578Hg} = +210°$ (c=1, CHCl₃) is employed. Yield: 81%, m.p. 180°–181° C. (yellowish crystals from ethyl acetate/methanol);

$[\alpha]^{22}_D = +84.2°$ (c=1, methanol).

The starting compounds (+)-cis-and (−)-cis-6-(4-aminophenyl)-8,9-dimethoxy-1,2,3,4,4a,10b-hexahydro-2-methyl-benzo[c][1,6]naphthyridine are known from EP-A-247 971.

COMMERCIAL USEFULNESS

The sulphonyl compounds according to the invention have pharmacological properties which render them commercially usable. They are distinguished above all by those properties which reveal them as being suitable for the therapy of diseases of the respiratory tract of various origins. In particular, inflammatory and allergen-induced bronchial diseases can be treated on the basis of the antiinflammatory and broncholytic activity of the compounds according to the invention. The compounds according to the invention are distinguished here by a very low toxicity, a wide therapeutic range, a long-lasting action and the absence of substantial side effects. The sulphonyl compound according to the invention additionally have antihypertensive properties.

The broncholytic and antiinflammatory activity of the sulphonyl compounds according to the invention enable them to be used in human and veterinary medicine, in which they are used for the treatment and prophylaxis of illnesses based on diseases of the bronchi. For example, acute and chronically obstructive diseases of the respiratory tract of various origins (bronchitis, allergic bronchitis, bronchial asthma) in humans and animals can be treated. On the basis of the antihypertensive activity, the compounds according to the invention can also be used for the treatment of hypertensive diseases of various origins and the associated concomitant diseases.

The invention thus furthermore relates to a method for the treatment of mammals, including humans, suffering from one of the abovementioned illnesses. The method is characterized in that a therapeutically active and pharmacologically tolerated amount of one or more of the compounds according to the invention is administered to the sick mammal.

The invention furthermore relates to the compounds according to the invention for use in the treatment and/or prophylaxis of the illnesses mentioned.

The invention likewise relates to the use of the compounds according to the invention for the preparation of medicaments which are employed for the treatment and/or prophylaxis of the illnesses mentioned.

The invention furthermore relates to medicaments for the treatment and/or prophylaxis of the illnesses mentioned, which contain one or more of the compounds according to the invention and/or their pharmacologically tolerated salts.

The medicaments according to the invention are prepared by processes which are known per se, reference being made, for example, to the statements in European Patent 163 965 with regard to formulations, dosages, and presentation forms. Inhalative administration, for which the compounds according to the invention appear to be outstandingly suitable on the basis of their action profile, is of particular importance in the treatment of bronchial diseases in this connection.

PHARMACOLOGY

The bronchospasmolytic action of the compounds according to the invention can be demonstrated on various in vitro and in vivo models. In the following table, the substances analyzed have been given numbers which correspond to the numbers of the substances in the examples.

BRONCHOSPASMOLYTIC ACTION AFTER I.T. INSTILLATION ON THE MODEL OF THE ANAESTHETIZED GUINEA PIG

The compounds according to the invention were investigated in more detail for their bronchospasmolytic action after i.t. instillation on the model of the anesthetized guinea pig as follows:

Animals

Male guinea pigs, Dunkin-Hartley, Charles-River/-Wiga, weight 300–450 g, N=6 animals per test group.

Method

Urethane anaesthesia; preparation of the v. jugularis for i.v. histamine administration; introduction of a Y-shaped tracheal catheter for measurement of the flow and for i.t. administration of the test substance; introduction of a blunt, short pleural catheter for measurement of the pleural pressure; determination of the lung function parameters of compliance and conductance (=1/resistance) by means of a Buxco lung function analyser; PC-assisted recording of the measurement data.

Triggering off of histamine-induced bronchospasms 20 and 10 min before and 2, 10, 30 and 60 min after administration of the substance; for the compliance and conductance, the baseline values before each bronchospasm and the delta-% changes during the bronchospasm are recorded by means of the PC program (T=4 sec); these data form the basis of the later evaluation.

Provocation solution: histamine 4 or 5 µg/kg (=22 or 27 nmol/kg) i.v. dissolved in 0.9% NaCl solution, administration volume 1 ml/kg, bolus injection; inclusion criterion: compliance decrease 70–90%. The test substances are ground in the wet state, if they are not water-soluble, and are administered in a dose of 3 µmol/kg in an application volume of 0.1 ml/kg i.t. 1% Tween 80 is added to the ready-to-administer suspension. A substance-free 10% succinyl-gelatine/aqua dist. solution containing 1% Tween 80 is used as the placebo solution by the same mode of administration and in the same administration volume.

Result

The percentage inhibition of the histamine-induced bronchoconstriction after i.t. administration of 3 µmol/kg substance in comparison with the placebo group is shown in the following Table 1. The average percentage bronchospasmolytic action over 60 min (act. 0–60), the maximum percentage bronchospasmolytic action (act. max) and the percentage bronchospasmolytic action at the time 60 min post appl. (act. 60) in each case in comparison with the corresponding placebo, have been calculated.

| Substance no. | Conductance | | | Compliance | | |
|---|---|---|---|---|---|---|
| | act. 0–60 | act. max | act. 60 | act. 0–60 | act. max | act. 60 |
| 1 | 55% | 61% | 51% | 34% | 37% | 35% |
| 2 | 61% | 84% | 60% | 47% | 72% | 40% |
| 9 | 57% | 71% | 51% | 56% | 70% | 45% |

We claim:
1. A compound of formula I

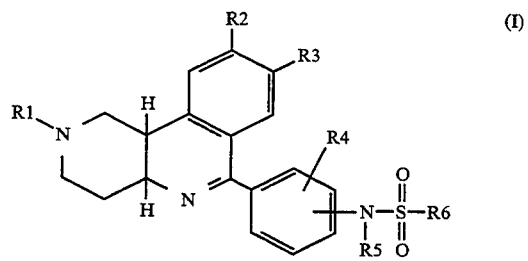

wherein
R1 denotes 1-4C-alkyl,
R2 denotes hydrogen (H), 1-4C-alkyl or 1-4C-alkoxy,
R3 denotes hydrogen (H), 1-4C-alkyl or 1-4C-alkoxy,
R4 denotes hydrogen (H), methyl or methoxy,
R5 denotes hydrogen (H) or 1-4C-alkyl and
R6 denotes 1-4C-alkyl, phenyl or substituted phenyl with one or two identical or different substituents selected from the group consisting of 1-4C-alkyl, 1-4C-alkoxy, hydroxyl and halogen,
or a salt thereof.

2. A compound of the formula I according to claim 1, in which
R1 denotes 1-4C-alkyl,
R2 denotes 1-4C-alkoxy,
R3 denotes 1-4C-alkoxy,
R4 denotes hydrogen or methyl,
R5 denotes hydrogen or 1-4C-alkyl and
R6 denotes 1-4C-alkyl, phenyl or substituted phenyl with one substituent selected from the group consisting of 1-4C-alkyl, 1-4C-alkoxy and halogen,
or a salt thereof.

3. A compound of formula I according to claim 1, in which
R1 denotes methyl,
R2 denotes methoxy,
R3 denotes methoxy and
R4 denotes hydrogen or methyl, the radical -N(R5)SO2R6 is in the 4-position of the phenyl radical bonded in the 6-position on the benzo-naphthyridine ring,
R5 denotes hydrogen, methyl or ethyl and
R6 denotes methyl, 4-methylphenyl, 4-methoxyphenyl or 4-fluorophenyl,
or a salt thereof.

4. A compound of claim: which is rac-cis-8,9-Dimethoxy-1,2,3,4,4a,10b-hexahydro-6-(4-methylsulphonamidophenyl)-2-methylbenzo[c][1,6]naphthyridine, or a salt thereof.

5. A compound of claim 1: which is rac-cis-8,9-Dimethoxy-1,2,3,4,4a,10b-hexahydro-2-methyl-6-[4-(p-toluenesulphonamido)-phenyl]-benzo[c][1,6]naphthyridine, or a salt thereof.

6. A compound of claim 1: which is (−)-cis-8,9-Dimethoxy-1,2,3,4,4a,10b-hexahydro-2-methyl-6-[4-(p- toluenesulphonamido)-phenyl]-benzo[c][1,6]naphthyridine, or a salt thereof.

7. A pharmaceutical composition comprising an effective amount of a compound of claim 1 and/or of a pharmacologically tolerated salt thereof, and pharmaceutically acceptable diluent or carrier therefor.

8. In a process for treating a disease of the bronchi which comprises administering an effective amount of an active ingredient to a mammal afflicted with said disease, the improvement wherein the active ingredient is a compound of claim 1 or a pharmacologically-tolerated salt thereof.

9. In a method of compounding a pharmaceutical composition comprising an active ingredient for the treatment of a disease of the bronchi, the improvement comprising incorporating in the composition a compound of claim 1, or a pharmacologically-tolerated salt thereof, as the active ingredient.

* * * * *

UNITED STATES PATENT AND TRADEMARK OFFICE
CERTIFICATE OF CORRECTION

PATENT NO. : 5,346,904

DATED : September 13, 1994

INVENTOR(S) : Dieter FLOCKERZI; Kurt KLEMM

It is certified that error appears in the above-indentified patent and that said Letters Patent is hereby corrected as shown below:

Column 2, line 16, "realate" should read --malate--; line 17, "aresonata" should read --amsonate--; line 18, "rosylate" should read --tosylate--; line 68, "rotation of" should read --rotation of $[\alpha]^{22}_{578Hg} = -213°$--. Column 3, lines 1 to 11, delete the entire text (formula). Column 10, line 1 (above the Table) insert (centered) --Table 1--, below which insert (centered) the title of the table --Percentage inhibition of the histamine-induced bronchoconstriction after i.t. administration of 3 μmol/kg substance in comparison with the placebo group.--; Column 10, line 59, "claim:" should read --claim 1:--

Signed and Sealed this

Seventeenth Day of January, 1995

Attest:

BRUCE LEHMAN

Attesting Officer

Commissioner of Patents and Trademarks